US009700433B2

(12) United States Patent
Myers

(10) Patent No.: US 9,700,433 B2
(45) Date of Patent: Jul. 11, 2017

(54) PATIENT-SPECIFIC ACETABULAR ALIGNMENT GUIDE AND METHOD

(71) Applicant: Reese Myers, Columbia City, IN (US)

(72) Inventor: Reese Myers, Columbia City, IN (US)

(73) Assignee: TECOMET, INC, Warsaw, IN (US)

( * ) Notice: Subject to any disclaimer, the term of this patent is extended or adjusted under 35 U.S.C. 154(b) by 826 days.

(21) Appl. No.: 14/089,932

(22) Filed: Nov. 26, 2013

(65) Prior Publication Data

US 2015/0148808 A1    May 28, 2015

Related U.S. Application Data

(60) Provisional application No. 61/730,931, filed on Nov. 28, 2012.

(51) Int. Cl.
*A61B 17/56* (2006.01)
*A61B 17/17* (2006.01)
*A61F 2/46* (2006.01)
*A61F 2/30* (2006.01)

(52) U.S. Cl.
CPC ........ *A61F 2/4609* (2013.01); *A61B 17/1746* (2013.01); *A61B 2017/568* (2013.01); *A61F 2/3094* (2013.01); *A61F 2002/4687* (2013.01)

(58) Field of Classification Search
CPC ............... A61F 2/4609; A61B 17/1746; A61B 2017/568
See application file for complete search history.

(56) References Cited

U.S. PATENT DOCUMENTS

| 2012/0041445 A1* | 2/2012 | Roose ................ A61B 17/1746 606/96 |
| 2012/0053590 A1* | 3/2012 | Allen ................. A61B 17/1746 606/87 |
| 2013/0018378 A1* | 1/2013 | Hananouchi ........... A61B 90/11 606/87 |

(Continued)

FOREIGN PATENT DOCUMENTS

| EP | 2491873 A2 | 8/2012 |
| WO | WO2012021858 A2 | 2/2012 |

(Continued)

OTHER PUBLICATIONS

International Search Report, ISA/FIPS, Mar. 13, 2014.

*Primary Examiner* — Nicholas Woodall
(74) *Attorney, Agent, or Firm* — AKC Patents, LLC

(57) ABSTRACT

A patient specific implant alignment guide assembly includes an anatomical reference component and a guide component. The anatomical reference component includes at least one matching feature shaped and dimensioned to match and complement a specific feature of an anatomic location. The anatomical reference component further has one or more protrusions and is fabricated based on one or more images of the anatomic location where the implant is to be implanted. The guide component includes one or more attachment protrusions that are shaped and dimensioned to match and interface with the one or more protrusions of the anatomical reference component. The guide component is attached to the anatomical reference component by matching and attaching the one or more attachment protrusions of the guide component to the one or more protrusions of the anatomical reference component.

14 Claims, 7 Drawing Sheets

(56) References Cited

U.S. PATENT DOCUMENTS

| | | | | |
|---|---|---|---|---|
| 2013/0035766 A1* | 2/2013 | Meridew | ............... | A61F 2/34 623/22.21 |
| 2014/0031722 A1* | 1/2014 | Li | ............... | A61F 2/4609 600/587 |
| 2014/0276870 A1* | 9/2014 | Eash | ............... | A61B 17/1746 606/91 |
| 2015/0012001 A1* | 1/2015 | Theiss | ............... | A61B 17/175 606/87 |

FOREIGN PATENT DOCUMENTS

| | | |
|---|---|---|
| WO | WO2012154407 A2 | 11/2012 |
| WO | WO2012158917 A1 | 11/2012 |

\* cited by examiner

PATIENT-SPECIFIC ACETABULAR ALIGNMENT GUIDE AND METHOD

CROSS REFERENCE TO RELATED CO-PENDING APPLICATIONS

This application claims the benefit of U.S. provisional application Ser. No. 61/730,931filed on Nov. 28, 2012 and entitled PATIENT-SPECIFIC ACETABULAR ALIGNMENT GUIDE AND METHOD, which is commonly assigned and the contents of which are expressly incorporated herein by reference.

FIELD OF THE INVENTION

The present invention relates to a patient-specific alignment guide for surgical implants and instruments and more particularly to a patient-specific alignment guide that includes an anatomical reference component and an implant or instrument positioning component.

BACKGROUND OF THE INVENTION

In several surgical procedures, diseased bone, tissue or organs are extracted and then implants are inserted to replace the extracted elements. Exact positioning and alignment of the implants is extremely critical and therefore in most cases alignment guides are used for the insertion of the implants. In particular, during hip replacement surgery, the placement and orientation of the hip implant within the acetabulum is extremely critical for the success of the procedure and the follow-up rehabilitation of the patient.

Accordingly, there is a need for devices and methods for placing accurately implants into a desired orientation and position within a patient's body.

SUMMARY OF THE INVENTION

The present invention relates to a patient-specific alignment guide that includes an anatomical reference component and an instrument positioning component.

In general, in one aspect, the invention features a patient specific implant alignment method including the following steps. First, obtaining one or more images of an anatomic location where an implant is to be implanted. Next, fabricating an anatomical reference component based on the one or more images. The anatomical reference component comprises at least one matching feature shaped and dimensioned to match and complement a specific feature of the anatomic location, and the anatomical reference component further comprises one or more protrusions. Next, inserting and attaching the anatomical reference component to the anatomic location so that the one matching feature of the anatomical reference component directly interfaces with the specific feature of the anatomic location. Next, providing a guide component comprising one or more attachment protrusions. The one or more attachment protrusions are shaped and dimensioned to match and interface with the one or more protrusions of the anatomical reference component. Next, attaching the guide component to the anatomical reference component by matching and attaching the one or more attachment protrusions of the guide component to the one or more protrusions of the anatomical reference component, and thereby aligning and orienting the guide component relative to the anatomical reference component. Next, verifying the positioning and alignment of the guide component relative to the anatomical reference component and the anatomic location. Next, attaching the guide component to the anatomic location and then using the guide component to align and insert the implant in the anatomic location.

Implementations of this aspect of the invention may include one or more of the following features. The anatomic location includes a cavity with a curved concave inner surface and the anatomical reference component comprises a curved concave cavity complementing and matching the curved concave inner surface of the anatomic location. Each of the one or more protrusions of the anatomical reference comprises a threaded opening matching a corresponding threaded opening in the corresponding matching attachment protrusion of the guide component. The one or more attachment protrusions of the guide component are attached to the one or more protrusions of the anatomical reference component with one of screws, clamps, pins or wires. The guide component is attached to the anatomic location with one of screws, clamps, pins or wires. The anatomic location is the acetabulum and the anatomical reference component includes a curved concave cavity area, a convex curved outer surface, a through opening and first and second protrusions extending from a bottom surface of the anatomical reference component and the a curved concave cavity area complements and matches the acetabulum anatomy. The guide component includes first and second slots on a top surface and the first and second protrusions of the anatomical reference component are shaped and dimensioned to slide within the first and second slots of the guide component. The guide component further comprises an upward extending cylindrical extension and wherein the cylindrical extension comprises a through-bore. The method further includes providing a positioning device and the positioning device comprises a rod dimensioned to be received within the through-bore of the cylindrical extension of the guide component, and the rod is a reference axis for the positioning device. The positioning device may be an implant positioning device or a surgical instrument positioning device. The method further includes providing a reference axis for positioning an implant or a device and the reference axis may be a pin, a reference frame or an electronic alignment device. The electronic alignment device may be an RF device, a laser beam or an optical beam. The one or more images may be computer tomography (CT) images, magnetic resonance imaging (MRI) images, ultrasound images, microwave images, Infrared images or radiographic images. The anatomical reference component is fabricated via additive layer machining The method may further include removing the anatomical reference component prior to inserting the implant in the anatomic location.

In general, in another aspect, the invention features a patient specific implant alignment guide assembly including an anatomical reference component and a guide component. The anatomical reference component comprises at least one matching feature shaped and dimensioned to match and complement a specific feature of an anatomic location, and the anatomical reference component further comprises one or more protrusions, and the anatomical reference component is fabricated based on one or more images of the anatomic location where the implant is to be implanted. The guide component includes one or more attachment protrusions and the one or more attachment protrusions are shaped and dimensioned to match and interface with the one or more protrusions of the anatomical reference component. The guide component is attached to the anatomical reference component by matching and attaching the one or more attachment protrusions of the guide component to the one or more protrusions of the anatomical reference component, and thereby the guide component is aligned and oriented relative to the anatomical reference component.

Among the advantages of this invention may be one or more of the following. The patient-specific alignment guide of this invention is configured to match the specific anatomy of the surgery site. It provides reliable alignment of implants and instruments used in the surgery site.

The details of one or more embodiments of the invention are set forth in the accompanying drawings and description bellow. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention relates to a patient-specific alignment guide that includes an anatomical reference component and an implant/instrument positioning component.

Figure 1A:
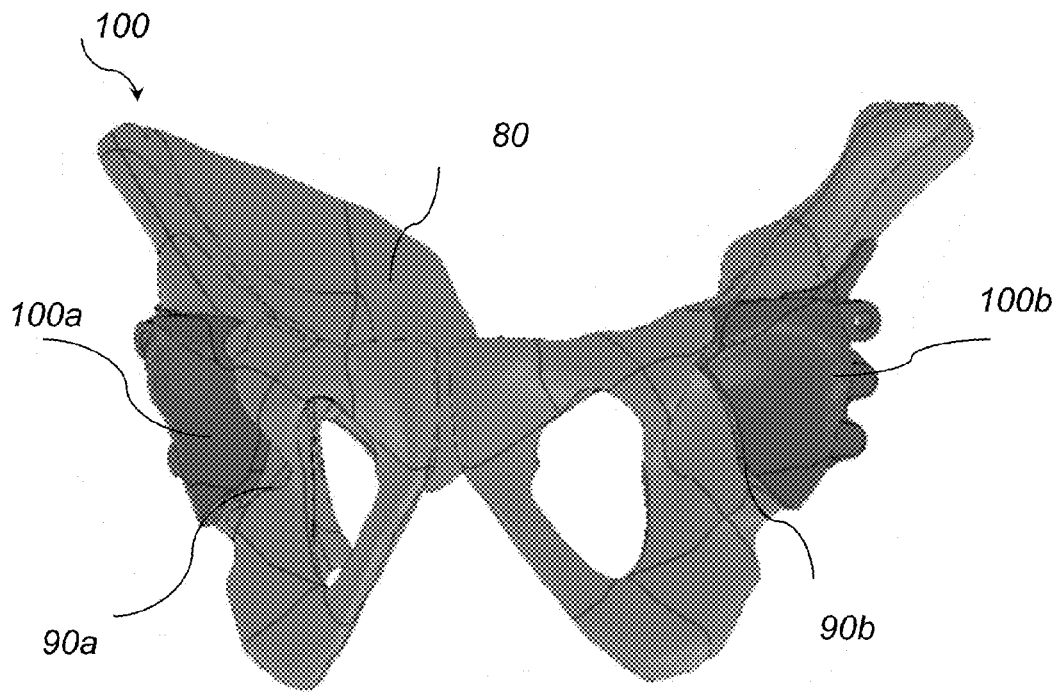
FIG. 1A is a schematic perspective view of a patient-specific acetabular alignment guide system of this invention.
Figure 1B:
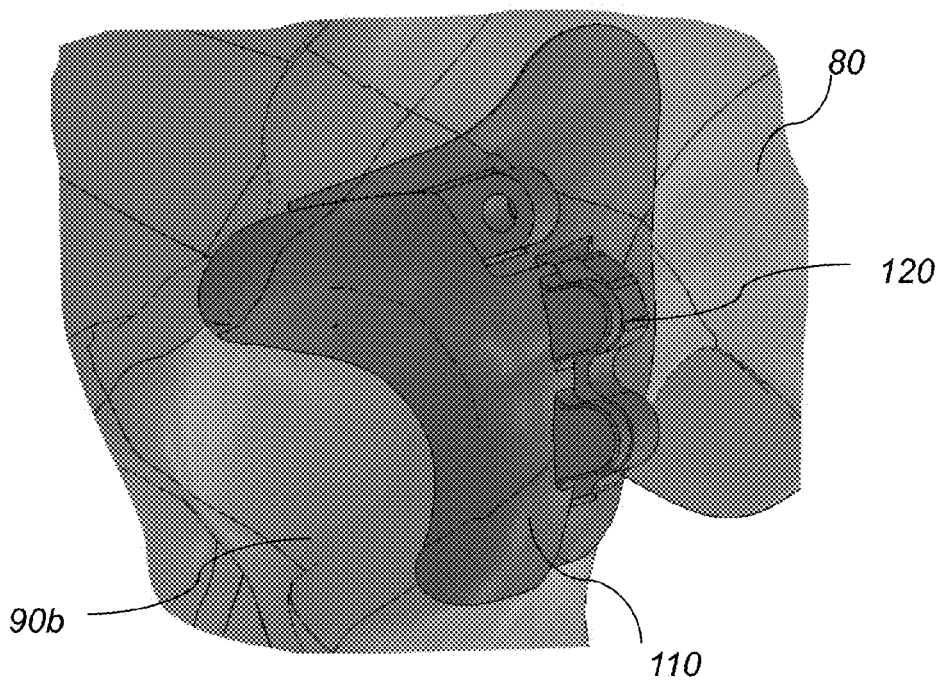
FIG. 1B is an enlarged view of the patient-specific acetabular alignment guide system of FIG. 1A.
Figure 2A:
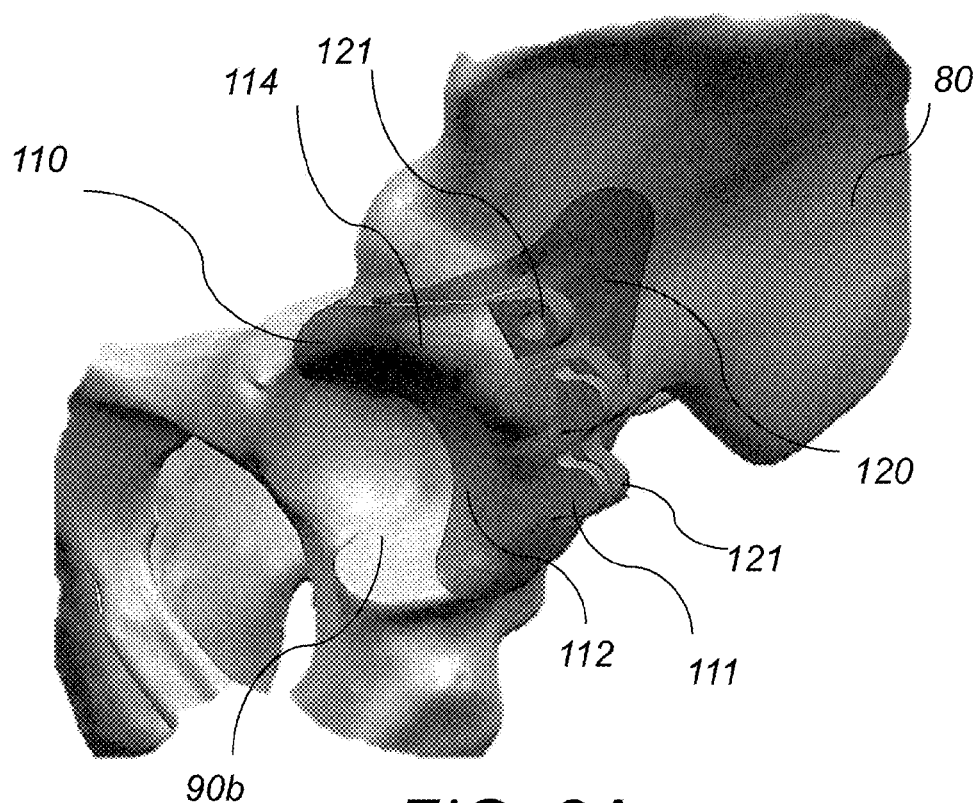
FIG. 2A depicts the first step in the method for applying the patient-specific acetabular alignment guide of this invention.
Figure 2B:
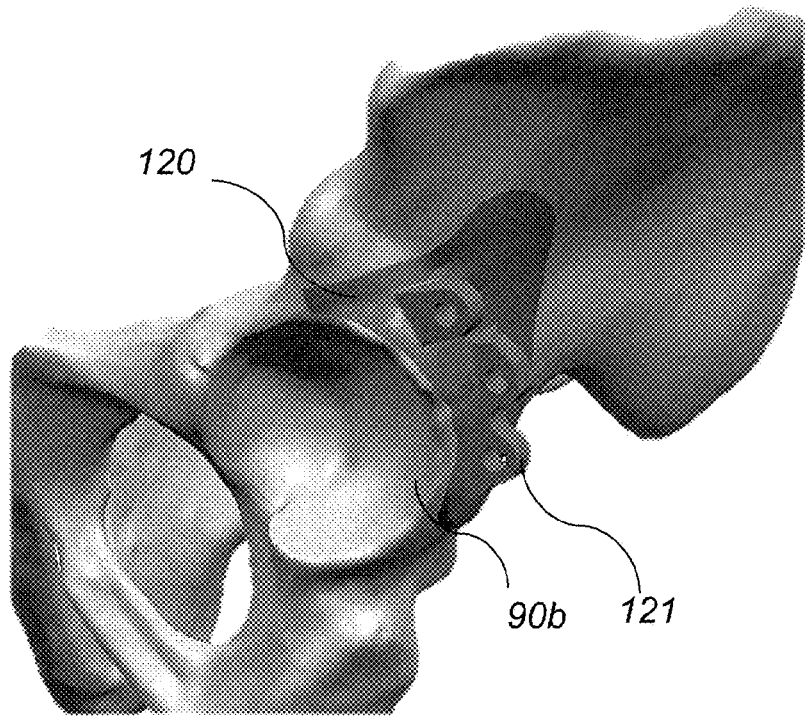
FIG. 2B depicts the second step in the method for applying the patient-specific acetabular alignment guide of this invention.
Figure 2C:
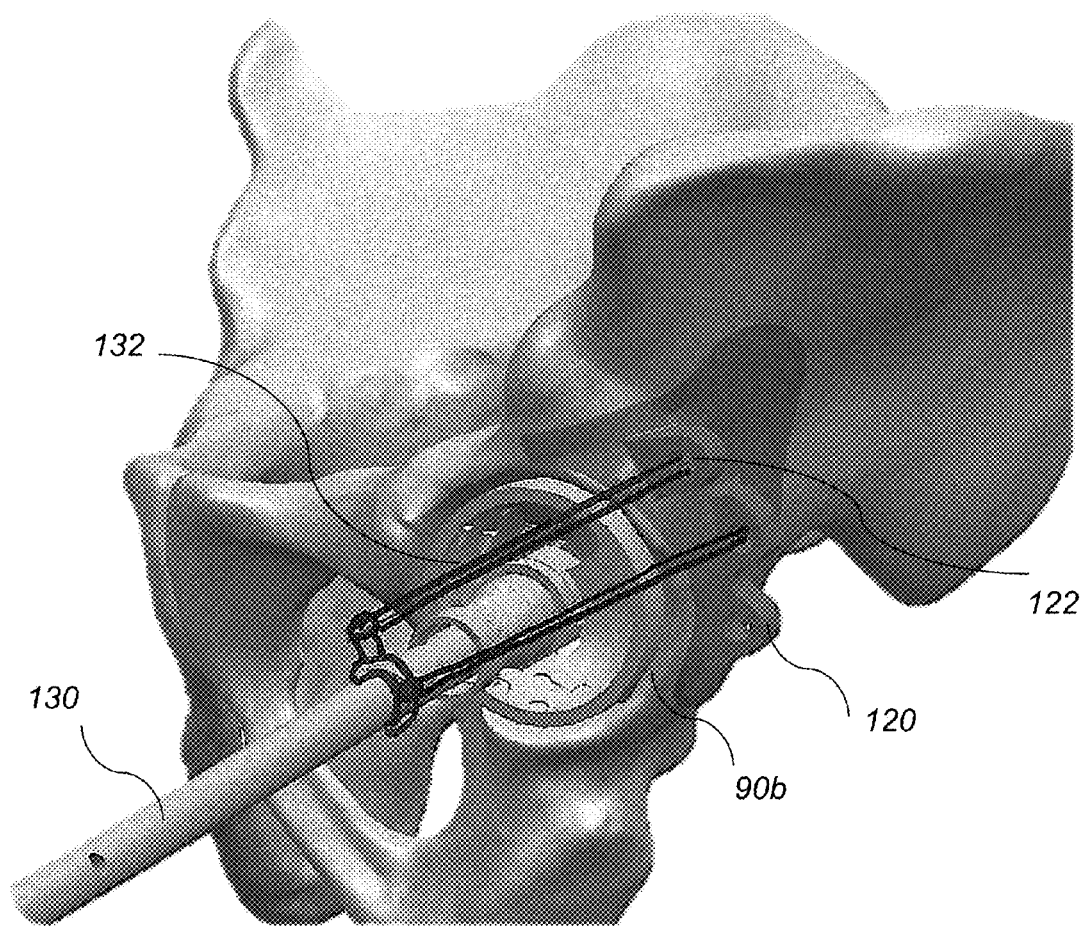
FIG. 2C depicts the third step in the method for applying the patient-specific acetabular alignment guide of this invention.

Referring to FIG. 1A and FIG. 1B, patient-specific acetabular alignment guide systems 100a, 100b are attached to the left acetabulum 90a and right acetabulum 90b, of pelvis 80 respectively. Each patient-specific alignment guide system includes a patient-specific anatomical reference component 110 and an instrument guide component 120. The anatomical reference component 110 is fabricated based on computed tomography (CT), magnetic resonance imaging (MRI), ultrasound imaging, microwave imaging, Infrared imaging or other radiographic studies of the patient's anatomy and is designed to match the patient's specific anatomic features. Next, the fabricated patient-specific anatomical reference component 110 is attached to the specific anatomic feature, i.e., the acetabulum 90b and then the instrument guide component 120 is attached to the anatomical reference component 110, as shown in FIG. 2A. This results in positioning the instrument guide component 120 in the accurate location and orientation. Once the accurate positioning of the guide component 120 is verified, the anatomical reference component 110 may be removed (as shown in FIG. 2B) and the appropriate instrument, device or implant is inserted and attached to the guide component 120, as shown in FIG. 2C. In this example, the anatomical reference component 110 is designed to match the acetabulum anatomy and it includes a convex curved outer surface 114, a concave cavity area 112 and protrusions 111 with threaded openings. The guide component 120 also includes protrusions 121 configured to be aligned with and attached to protrusions 111 of component 110. Protrusions 121 of component 120 are attached to protrusions 111 of component 110 with screws, clamps, pins, or wires, among others.

Figure 3A:
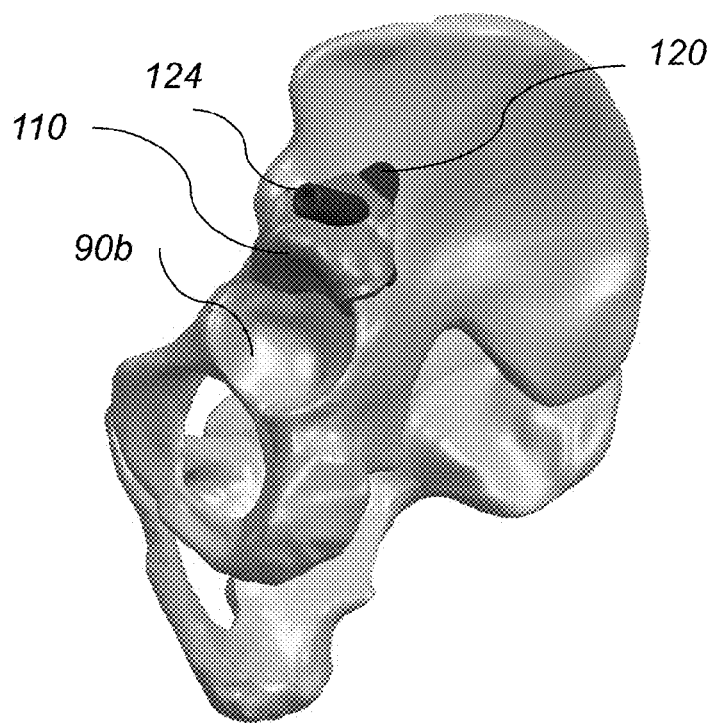
FIG. 3A depicts the first step in the method for applying another embodiment of a patient-specific acetabular alignment guide of this invention.
Figure 3B:
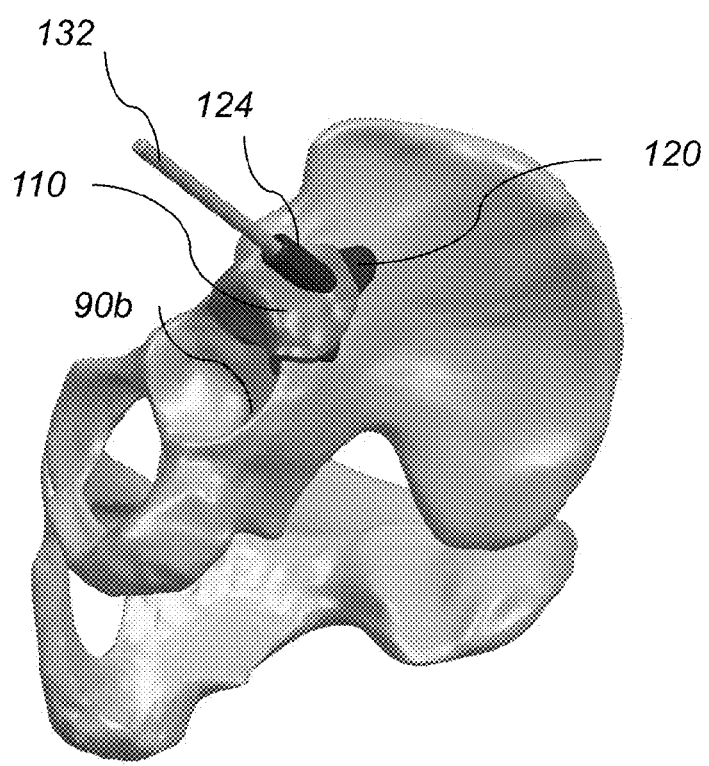
FIG. 3B depicts the second step in the method for applying the embodiment of the patient-specific acetabular alignment guide of FIG. 3A.
Figure 3C:
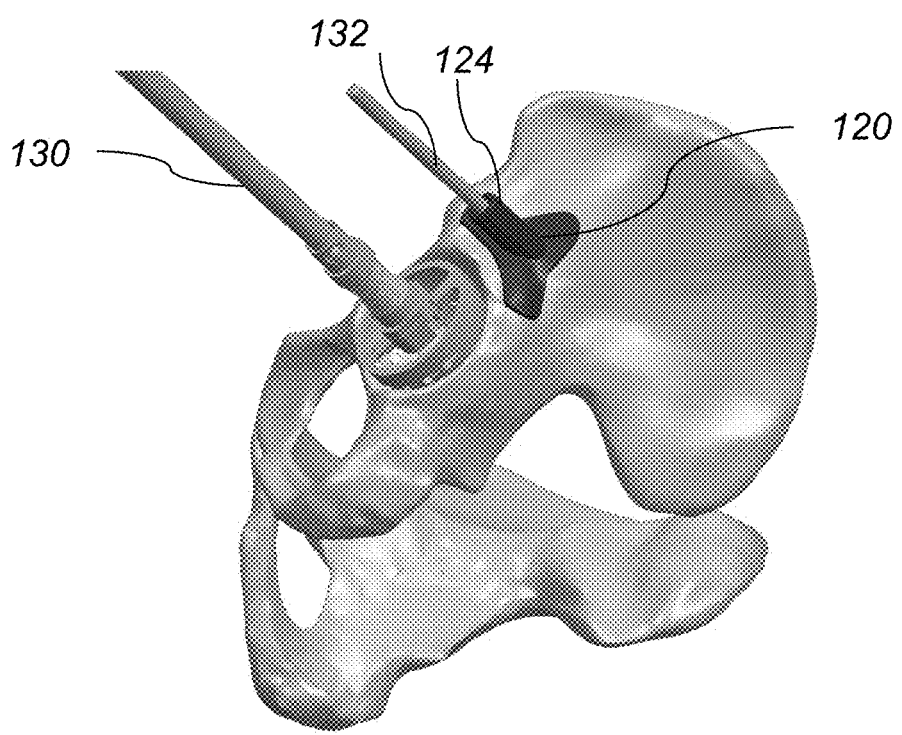
FIG. 3C depicts the third step in the method for applying the embodiment of the patient-specific acetabular alignment guide of FIG. 3A.
Figure 4A:
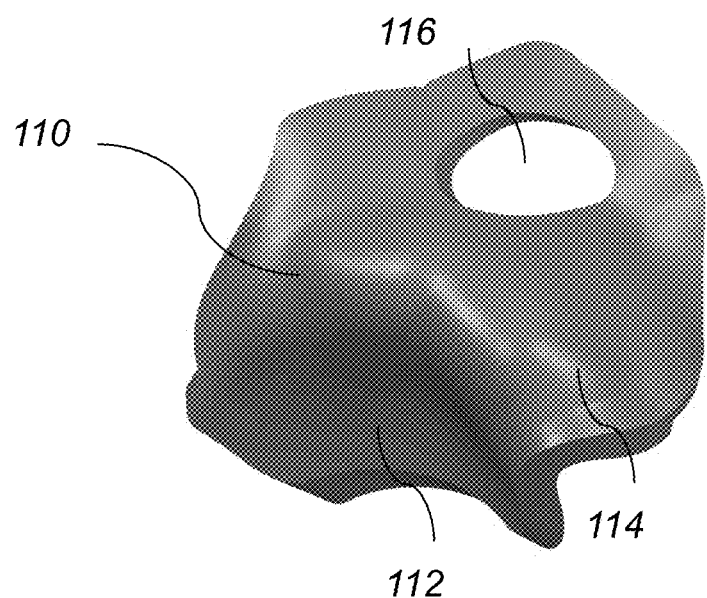
FIG. 4A depicts a top view of the anatomic reference component of the patient-specific acetabular alignment guide of FIG. 3A.
Figure 4B:
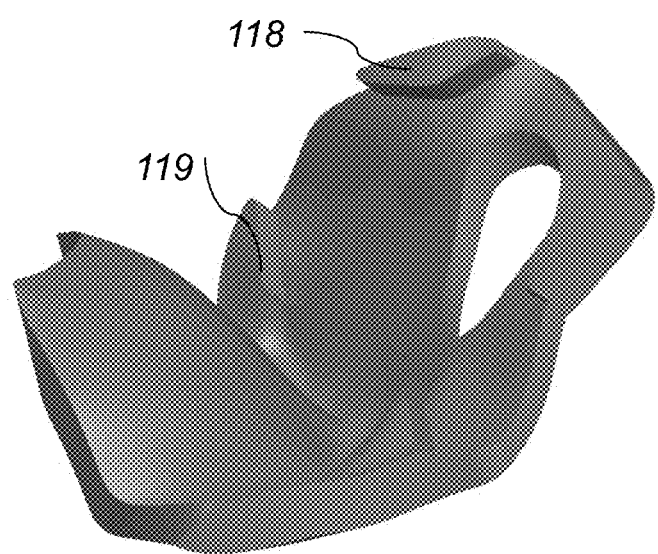
FIG. 4B depicts a bottom view of the anatomic reference component of the patient-specific acetabular alignment guide of FIG. 3A.
Figure 5:
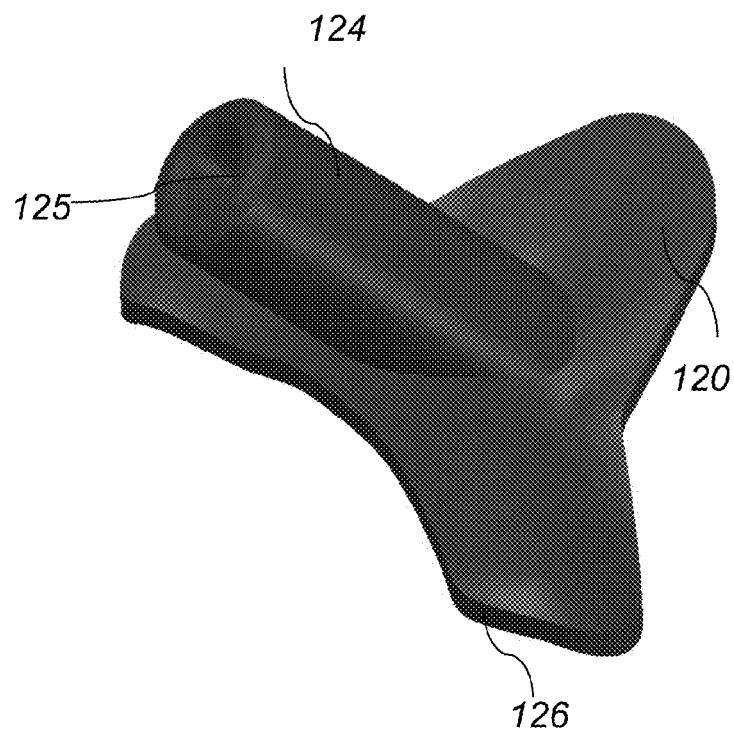
FIG. 5 depicts a top perspective view of the instrument guide component of the patient-specific acetabular alignment guide of FIG. 3A.
Figure 6:
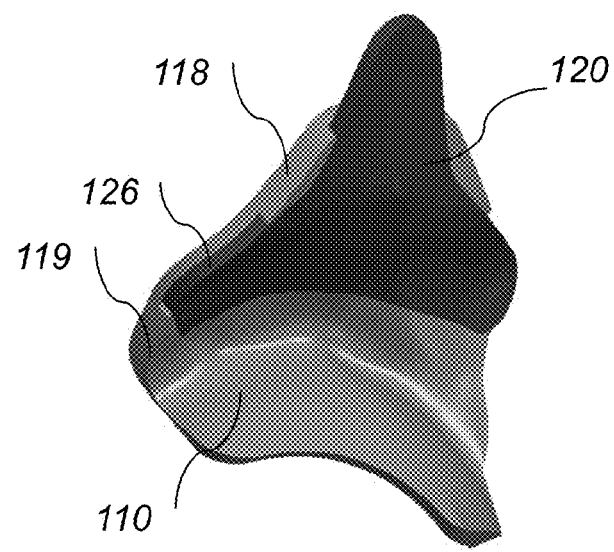
FIG. 6 depicts a bottom perspective view of the patient-specific acetabular alignment guide of FIG. 3A.

Referring to FIG. 3A, FIG. 4A-FIG. 6, in another embodiment, the anatomical reference component 110 is designed to match the acetabulum anatomy and it includes a convex curved outer surface 114, a concave cavity area 112 and a through opening 116, as shown in FIG. 4A. The bottom surface of component 110 includes protrusions 118, 119 designed to match corresponding slots in the guide component top surface, as shown in FIG. 4B. As shown in FIG. 6, guide component 120 includes a protrusion 126 that slides and locks between protrusions 119 and 118 of reference component 110. In this embodiment, guide component 120 includes an upward extending cylindrical protrusion 124 having a through-bore 125. Through-bore 125 is dimensioned to receive rod 132 of the positioning device 130, as shown in FIG. 2C and FIG. 3C. Rod 132 is used as a reference axis for positioning device 130. In other embodiments, reference axis 132 may be a pin, a reference frame or an electronic alignment device, such as an RF device, a laser beam or an optical beam. In yet other embodiments, more than one patient-specific acetabular alignment guide systems are used and they are attached to different attachment locations. Device 130 may be an implant positioning device or a surgical instrument such as a reaming or a drilling tool.

In operation, anatomical reference component 110 is designed to match a specific anatomic feature of the patient and is approved by a physician. Next, the anatomical reference component 110 is machined using conventional methods or is generated via an additive layer machining method. Next, anatomical reference component 110 is sterilized via any acceptable method and is delivered to the operating area. After exposing the acetabulum, the surgeon places the patient-specific anatomical reference component 110 into the acetabulum, where it settles into a unique predetermined position. Next, the guide component 120 is attached to the anatomical reference component 110 and to the pelvis 80. Guide component 120 is attached to the pelvis via screws, clamps, pins or wires, among others. There may be one or more attachment locations. Next, the instrument positioning component 132 is attached to a mating feature of the guide component 120. At this point, the anatomical reference component 110 may be removed, if it obscures the surgical location. When performing critical positioning processes during the operation, the surgeon can align the instrument or implant with the instrument positioning component 132. The alignment may be visual or via a direct connection. After the operation is completed, the components are removed and discarded.

Several embodiments of the present invention have been described. Nevertheless, it will be understood that various modifications may be made without departing from the spirit and scope of the invention. Accordingly, other embodiments are within the scope of the following claims.

What is claimed is:

1. A patient specific implant alignment method comprising:
   obtaining one or more images of an anatomic location where an implant is to be implanted;
   fabricating an anatomical reference component based on the one or more images, wherein the anatomical reference component comprises at least one matching feature shaped and dimensioned to match and complement a specific feature of the anatomic location, and wherein the anatomical reference component further comprises one or more protrusions;
   inserting and attaching the anatomical reference component to the anatomic location so that the one matching feature of the anatomical reference component directly interfaces with the specific feature of the anatomic location;
   providing a guide component comprising one or more attachment protrusions and wherein the one or more attachment protrusions are shaped and dimensioned to match and interface with the one or more protrusions of the anatomical reference component;
   attaching the guide component to the anatomical reference component by matching and attaching the one or more attachment protrusions of the guide component to the one or more protrusions of the anatomical reference component, and thereby aligning and orienting the guide component relative to the anatomical reference component;
   verifying the positioning and alignment of the guide component relative to the anatomical reference component and the anatomic location;
   attaching the guide component to the anatomic location; and
   using the guide component to align and insert the implant in the anatomic location; and
   wherein the anatomic location comprises the acetabulum and wherein the anatomical reference component comprises a curved concave cavity area, a convex curved outer surface, a through opening and first and second protrusions extending from a bottom surface of the anatomical reference component and wherein the a curved concave cavity area complements and matches the acetabulum anatomy.

2. The method of claim 1, wherein the anatomic location comprises a cavity with a curved concave inner surface and wherein the anatomical reference component comprises a curved concave cavity complementing and matching the curved concave inner surface of the anatomic location.

3. The method of claim 1, wherein each of the one or more protrusions of the anatomical reference comprises a threaded opening matching a corresponding threaded opening in the corresponding matching attachment protrusion of the guide component.

4. The method of claim 1, wherein the one or more attachment protrusions of the guide component are attached to the one or more protrusions of the anatomical reference component with one of screws, clamps, pins or wires.

5. The method of claim 1, wherein the guide component is attached to the anatomic location with one of screws, clamps, pins or wires.

6. The method of claim 1, wherein the guide component comprises first and second slots on a top surface and wherein the first and second protrusions of the anatomical reference component are shaped and dimensioned to slide within the first and second slots of the guide component.

7. The method of claim 1, wherein the guide component further comprises an upward extending cylindrical extension and wherein the cylindrical extension comprises a through-bore.

8. The method of claim 7, further comprising providing a positioning device and wherein the positioning device comprises a rod dimensioned to be received within the through-bore of the cylindrical extension of the guide component, and wherein the rod is a reference axis for the positioning device.

9. The method of claim 8, wherein the positioning device comprises an implant positioning device or a surgical instrument positioning device.

10. The method of claim 1, further comprising providing a reference axis for positioning an implant or a device and wherein the reference axis comprises one of a pin, a reference frame or an electronic alignment device.

11. The method of claim 10, wherein the electronic alignment device comprises one of an RF device, a laser beam or an optical beam.

12. The method of claim 1 wherein the one or more images comprise one of computer tomography (CT) images, magnetic resonance imaging (MRI) images, ultrasound images, microwave images, Infrared images or radiographic images.

13. The method of claim 1 wherein the anatomical reference component is fabricated via additive layer machining.

14. The method of claim 1, further comprising removing the anatomical reference component prior to inserting the implant in the anatomic location.

* * * * *